_(12)_ United States Patent
Winkelaar et al.

(10) Patent No.: US 7,410,556 B1
(45) Date of Patent: Aug. 12, 2008

(54) PURIFICATION OF AQUEOUS SOLUTIONS OF ORGANIC ACIDS

(75) Inventors: Hendrik Martinus Winkelaar, Hilversum (NL); Jan Van Breugel, Woudrichem (NL); Margarita Camprubi Vila, Sabadell (ES); Jose Maria Vidal Lancis, Vilasser De Mar (ES)

(73) Assignee: Purac Biochem B.V., Gorinchem (NL)

( * ) Notice: Subject to any disclaimer, the term of this patent is extended or adjusted under 35 U.S.C. 154(b) by 386 days.

(21) Appl. No.: 10/130,990

(22) PCT Filed: Nov. 27, 2000

(86) PCT No.: PCT/NL00/00865

§ 371 (c)(1),
(2), (4) Date: Oct. 1, 2002

(87) PCT Pub. No.: WO01/38283

PCT Pub. Date: May 31, 2001

(30) Foreign Application Priority Data

Nov. 26, 1999 (NL) .................................. 1013682

(51) Int. Cl.
*B01D 3/10* (2006.01)
*B01D 3/28* (2006.01)
*C07C 51/44* (2006.01)
*B01D 1/22* (2006.01)

(52) U.S. Cl. .................. 203/14; 159/49; 159/DIG. 16; 203/15; 203/72; 203/78; 562/580

(58) Field of Classification Search ............ 203/4, 203/14, 15, 72, 73, 78, 89, 98; 562/580, 562/589; 159/49, 62, 901, DIG. 8, DIG. 16
See application file for complete search history.

(56) References Cited

U.S. PATENT DOCUMENTS 1,594,843 A    8/1926    Lawrie (Continued)

FOREIGN PATENT DOCUMENTS

BE    1 008 099 A    1/1996

(Continued)

OTHER PUBLICATIONS

International Search Report for PCT/NL 00/00865, dated Apr. 27, 2001.

*Primary Examiner*—Virginia Manoharan
(74) *Attorney, Agent, or Firm*—Gilberto M. Villacorta; Sunit Talapatra; Foley & Lardner LLP

(57) ABSTRACT

The invention relates to a method and a device for the purification of an aqueous solution of an organic acid having a boiling point at atmospheric pressure of less than 450° C., which further has approximately 275 g carboxylate ions/l or less, preferably 250 g carboxylate ions/l or less, and preferably less than 1% by weight ionic impurities, calculated on the basis of the total solution. In particular, the invention relates to a method and a device for the continuous purification and concentration, on an industrial scale, of an aqueous solution of an organic acid having a boiling point at atmospheric pressure of less than 450° C. According to the method, this solution is subjected to two or more distillation steps, the first distillation step being carried out at a temperature of from 80° to 150° C. and a pressure of from 50 to 250 mbar, and the second distillation step being carried out at a temperature of from 80° to 200° C. and a pressure of from 0.01 to 50 mbar.

26 Claims, 5 Drawing Sheets

U.S. PATENT DOCUMENTS

| | | | |
|---|---|---|---|
| 3,721,610 A * | 3/1973 | Chaintron | 203/77 |
| 4,219,389 A * | 8/1980 | Biola et al. | 203/72 |
| 4,601,790 A * | 7/1986 | Stage | 203/6 |
| 4,867,849 A * | 9/1989 | Cova et al. | 203/28 |
| 5,370,774 A * | 12/1994 | Kuenstle et al. | 203/6 |
| 5,660,691 A * | 8/1997 | Barnicki et al. | 203/72 |
| 5,750,007 A * | 5/1998 | Clode et al. | 203/3 |
| 5,750,732 A * | 5/1998 | Verser et al. | 549/274 |
| 6,048,441 A * | 4/2000 | Auer et al. | 203/72 |
| 6,326,458 B1 * | 12/2001 | Gruber et al. | 528/354 |
| 6,489,508 B1 * | 12/2002 | Van Gansbeghe et al. | 562/589 |
| 6,509,179 B1 * | 1/2003 | Veldhuis-Stribos et al. | 435/139 |
| 6,630,603 B1 * | 10/2003 | Van Breugel et al. | 562/580 |
| 6,706,898 B2 * | 3/2004 | Sumner, Jr. | 549/413 |
| 6,982,026 B2 * | 1/2006 | Cockrem et al. | 203/2 |

FOREIGN PATENT DOCUMENTS

| | | |
|---|---|---|
| WO | WO 98 55442 A | 12/1998 |

* cited by examiner

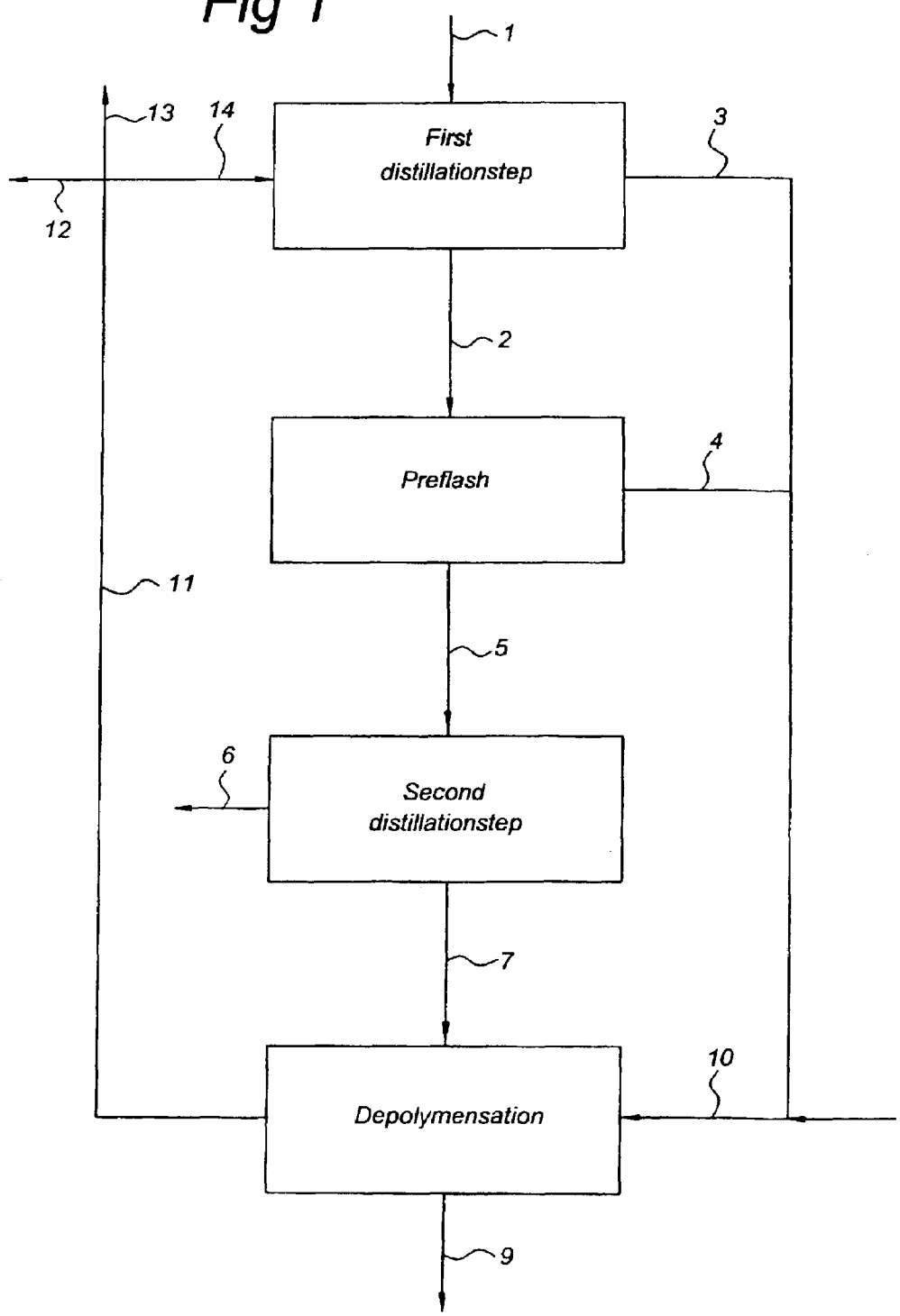

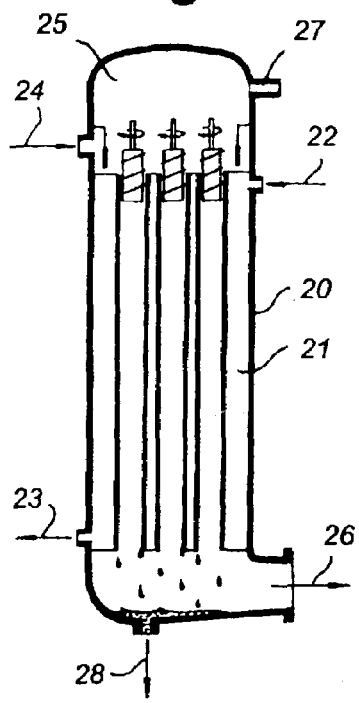
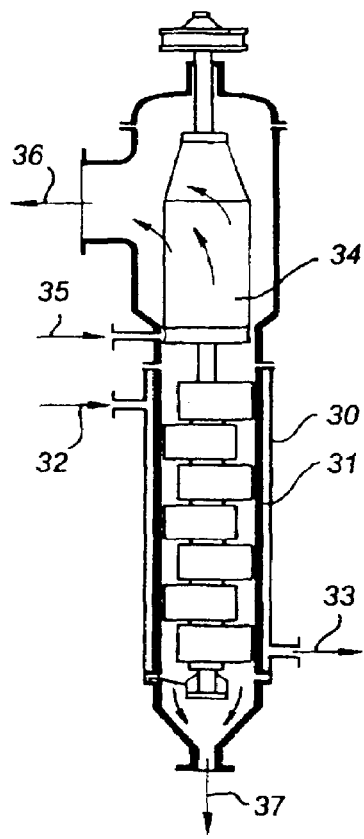
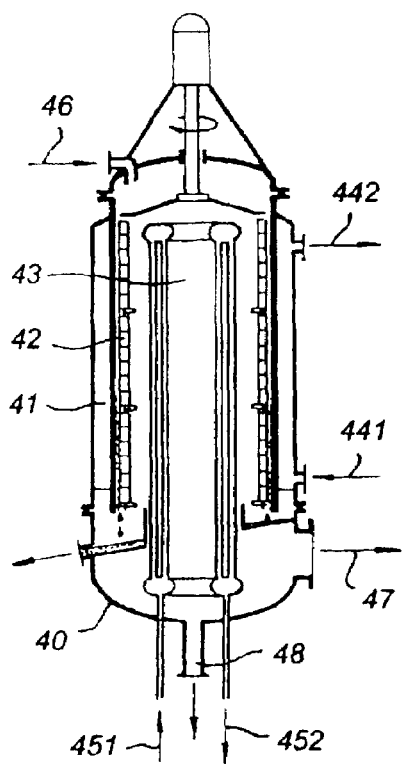

PURIFICATION OF AQUEOUS SOLUTIONS OF ORGANIC ACIDS

SUMMARY OF THE INVENTION

The invention relates to a method and a device for the purification of an aqueous solution of an organic acid having a boiling point at atmospheric pressure of less than 450° C., which comprises approximately 275 g carboxylate ions/1 or less, preferably 250 g carboxylate ions/1 or less, and preferably less than 1% by weight ionic impurities, calculated on the basis of the total solution, and in particular to a method and a device for the continuous purification and concentration, on an industrial scale, of an aqueous solution of an organic acid having a boiling point at atmospheric pressure of less than 450° C. The method and the device according this invention can also be employed for the production and purification of cyclic dimers of said organic acids, provided that said cyclic dimers have a boiling point at atmospheric pressure of less than 450° C.

In the context of the invention, the organic acid includes monocarboxylic, dicarboxylic and polycarboxylic acids. Moreover, the term organic acid is to be construed as comprising the pure acid as well as a mixture of substantially pure acid and optionally a small amount of oligomerized or polymerized organic acid and/or cyclic dimers of the organic acid. Examples of these organic acids are citric acid, glycolic acid, acetic acid, acrylic acid, methacrylic acid, etc. The organic acid is preferably an α-hydroxy acid and in particular lactic acid. Likewise, the terms α-hydroxy acid and lactic acid are understood as meaning a mixture of substantially unpolymerized α-hydroxy acid or unpolymerized lactic acid and possibly a small amount of polymerized α-hydroxy acid and the cyclic form of the dimer, or lactic acid and dilactide (the cyclic form of the dimer).

THE PRIOR ART

W/O 98/55442 describes a method for the purification of laxtic acid of this type in which a solution of lactic acid in water as is obtained from fermentation or a different source is subjected to at least three steps. The first step comprises the removal of ionic substances which may catalyse the oligomerization of lactic acid from the aqueous solution of lactic acid, the solution containing less than 80%, preferably less then 50%, and in particular less than 30% lactic acid. Preferably, a cation exchanger is used to remove cationic substances, and then an anion exchanger is used to remove anionic substances. The second step comprises concentrating the solution to a concentration of 50 to 90%, preferably 70 to 90%, by evaporation under reduced pressure, the pressure being 50 to 500 mbar and preferably 50 to 250 mbar and the temperature being kept as low as possible. The evaporation is preferably carried out with the aid of flowing film evaporation. The third step comprises a distillation at a pressure of from 0.001 to 100 mbar, preferably 0.1 to 20 mbar, and in particular 1 to 10 mbar, the temperature of the wall of the evaporation device being 80° to 160° C. and preferably 110° to 160° C. The distillation is preferably carried out with the aid of a mechanically moved thin film evaporator or a short path evaporator and provides pure lactic acid. If appropriate, a post-concentration step may be carried out between the second and third steps. This post-concentration is also preferably carried out using a mechanically moved thin film evaporator or a short path evaporator, at a pressure of from 10 to 500 mbar, preferably 50° to 250 mbar, and at a temperature of from 50° to 150° C., preferably from 80 to 120° C. It is claimed that in this post-concentration the concentration of the solution as obtained from the first concentration step (step two) can be raised to 100% lactic acid.

One drawback of this method is that in the first concentration step (step two) the separation between the solution containing concentrated lactic acid and the fraction which contains substantially water is poor, and consequently the fraction which contains substantially water also contains a significant amount of lactic acid and impurities which has an adverse effect on the yield of the method. Moreover, this water-containing fraction has to be cleaned before it can be discharged or recycled into the method. Another drawback of this method is the sudden fall in pressure (from the first to the second concentration step). This disturbance to the liquid phase reduces the quality in the second concentration step, particularly if the concentrate from the first concentration step contains dissolved gases or water. A disadvantage of a short path evaporator is that during operation splashing of the residual product against the internal condenser occurs.

Other methods for the purification of organic carboxylic acids such as lactic acid are described in French patent specification 1.290.212 and U.S. Pat. No. 1,594,843. The French patent specification describes the use of ion exchangers for removing cationic substances, U.S. Pat. No. 1,594,843 describes the purification of an aqueous solution of lactic acid, during which a thin film evaporator is used, operated under a vacuum of 27 inches of mercury or greater and a temperature of 450° to 600° F. These conditions correspond to a pressure of approximately 436 mbar or lower and a temperature of approximately 232° to 316° C. These methods provide lactic acid of insufficient purity.

Example 1 of Belgium patent 9400242 describes the short path distillation of lactic acid on a laboratory scale (the device used is a lab scale device with an evaporation and condensation surface area of 0.06 m$^2$ and a throughput of approximately 0.04 to 5 kg/h). The pressure was varied between 50 and 130 mbar, the temperature of the film was varied between 100 and 125° C., and the flow rate was varied between 325 and 1150 g/h. The yield varied from 62 to 95%, the highest yield having been obtained at a pressure of 50 mbar, a film temperature of 100° C. and a flow rate of 1150 g/h.

DETAILED DESCRIPTION OF THE INVENTION

The object of the present invention is to resolve the drawbacks of the methods according to the prior art. The present invention therefore relates to a method for the purification of an aqueous solution of an organic acid having a boiling point at atmospheric pressure of less than 450° C., preferably an α-hydroxy acid and in particular lactic acid, which comprises approximately 275 g carboxylate ions/1 or less, preferably 250 g carboxylate ions/1 or less, and preferably less than 1% by weight, preferably less than 0.1% by weight, and in particular 0.001 to 0.01% by weight ionic impurities, calculated on the basis of the total solution, the solution being subjected to two or more distillation steps. This method can also be used for the production and purification of cyclic dimers of the organic acid, provided that the boiling point of the dimer is less than 450° C. The organic acid is preferably an α-hydroxy acid and in particular lactic acid. One advantage of this method is that in the first distillation step, during which the organic acid concentration is increased to at least 95% by weight organic acid, calculated on the basis of the weight of the product of this first distillation step, an aqueous fraction is obtained which contains less than 1% by weight organic acid, so that this aqueous fraction can be discharged or recycled into the method without further cleaning.

According to the invention, the aqueous solution is preferably distilled at reduced pressure in a first distillation step at a temperature of from 80° to 150° C. in particular from 100° to 140° C., and at a pressure of from 50 to 250 mbar, in particular from 60 to 150 mbar. However, if the pressure is lower than 50 mbar, it is necessary to use cooling water at a temperature of lower than ambient temperature (25° C.) in order to condense the water vapor released, which has an adverse effect on the process management and process economy.

In the first distillation step, the aqueous solution is brought into the vapour phase by means of film evaporation. This film evaporation can be achieved using one or more falling film evaporators, wiped film evaporators and/or thin film evaporators. Evaporation devices of this type are known in the prior art and are described, for example, in Kirk-Othmer, Encyclopaedia of Chemical Technology, fourth edition, Volume 9, pp. 959-981 (1994). Then, the vapour is preferably paused to a first distillation column, in which separation into two fractions is carried out under reflux conditions. In this way, a first top fraction is obtained, which substantially comprises water and contains no more than 1% by weight, preferably no more than 0.1% by weight organic acid, calculated on the basis of the weight of the top fraction, and a first bottom fraction (product) which contains at least 95% by weight, preferably 99 to 99.9% by weight Total Organic Acid (TOA), calculated on the basis of the weight of the bottom fraction. It will be clear to the person skilled in the art that it is desirable for the first bottom fraction to contain the maximum possible amount of Total Organic Acid. Therefore, the first bottom fraction may consist of 100% by weight organic acid. It will also be clear to the person skilled in the art that a plurality of distillation columns can be used in the first distillation step.

Total Organic Acid (TOA) content is de acid content after hydrolysis of intermolecular ester bonds by using excess base and is determined by backtitration with acid. The Total Organic Acid content gives therefore the amount of monomeric acid, (cyclic and/or linear) dimeric acid, oligomeric acid and polymeric acid. The Free Organic Acid (FOA) content is determined by a direct titration with a base, i.e. prior to the hydrolysis of the intermolecular ester bonds. The content of Monomeric Organic Acid (MOA) is here defined as:

MOA=TOA−2×(TOA−FOA)

provided that TOA−FOA<10%.

The first distillation column which is used in the first step preferably has a plate number of from 0.1 to 10, preferably 1 to 10 and in particular 1 to 5.

The product of the first distillation step is then distilled in a second distillation step, preferably under vacuum, forming a top fraction, which contains at least 99.5% by weight pure Total Organic Acid, and a distillation residue (bottom fraction). In the context of the invention, under vacuum is to be understood as meaning a pressure of from 0.01 to 50 mbar, more preferably 0.1 to 20 mbar, in particular 1 to 10, and more in particular 2 to 10 mbar. In this second step, the temperature is preferably 80° to 200° C., more preferably 100° to 200° C., in particular 100° C. to 140° C. and more in particular 110° to 140° C. The second distillation step is preferably carried out in one or more short path distillation devices, but in particular in one or more vacuum distillation units which do not have the disadvantage of splashing as outlined above.

According to a more preferred embodiment of the invention, in the second distillation step the product from the first distillation step is brought into the vapour phase by means of film evaporation, and then the vapour is passed to a second distillation column, separation into two fractions being brought about under reflux conditions. In this more preferred embodiment, the product (the first bottom fraction) from the first distillation step is brought into the vapour phase preferably by using one or more falling film evaporators, wiped film evaporators and/or thin film evaporators. The second distillation column preferably has a plate number of from 0.1 to 10, more preferably 1 to 10, and in particular from 1 to 5. In this way, a second top fraction (product) is obtained, which substantially comprises the organic acid and which contains at least 99.5% by weight Total Organic Acid. The residue (the second bottom fraction) of this second distillation step contains substantially sugars and products derived therefrom, some monomeric organic acid, remainder dimers, trimers and oligomers of the organic acid, cyclic dimers of the organic acid (hence, dilactide when the organic acid is lactic acid) and other non-volatile components. It will be clear to the person skilled in the art that a plurality of distillation columns can be used in the second distillation step. This more preferred embodiment of the second distillation step is preferably carried out under a pressure and at a temperature which are the same as those indicated above where one or more short path distillation devices can be used. If very pure organic acid is desired, the top fraction obtained using this more preferred embodiment can be subjected to a distillation under vacuum as described above.

According to the invention, it is preferable for the product from the first distillation step (the first bottom fraction) to be subjected to a conditioning step (so-called "preflash") before it undergoes a second distillation step, the pressure in this conditioning step preferably being the same as that used in the second distillation. However, the pressure may also be higher i.e. at most 50 mbar (the lowest pressure that can be used in the first distilling step) and preferably at most 20 mbar, and at least 10 mbar (the highest pressure that can be used in the second distillation step). This preferred embodiment has the advantage that a residual quantity of water and dissolved gases are removed before the product is subjected to the second distillation step. For example, the product from the fist distillation step may contain, for example 96% by weight lactic acid, the use of a preflash allowing the lactic acid content to be increased to, for example 99% by weight, so that in the second distillation step it is possible to obtain purer lactic acid and to achieve more stable operation. The fraction of water which is removed using a preflash generally contains 10 to 50%, preferably 10 to 20% by weight Total Organic Acid.

The residue of the second distillation step can be recycled into the method, purged, or processed in the same method but on a smaller scale (this requires a second distillation section), but is preferably first subjected to a depolymerization step, in particular because the residue contains approximately 1% by weight Total Organic Acid, non-volatile remainder dimer, oligomers and polymers of the acid and the cyclisized form of the dimer (e.g., dilactide when the acid is lactic acid), calculated on the basis of the total residue, and sugars. It will be obvious to the person skilled in the art that such a depolymerization step can be omitted if the organic acid does not contain reactive groups that may give rise to dimerization, oligomerization of polymerization such as is the case when the organic acid is acetic acid.

The depolymerization step is preferably carried out by heating a mixture comprising 30 to 70% by weight, preferably 40 to 60% by weight, of an aqueous stream which preferably contains 80 to 100% by weight water, and 70 to 30% by weight, preferably 60 to 40% by weight, of the residue of the second distillation step at a temperature of from 60° to 100°

C. for from 1 to 30, preferably 1 to 10 hours under atmospheric pressure. This aqueous stream is preferably taken from the first distillation step and/or the preflash. The product from the depolymerization step is preferably recycled to the first distillation step, is purged or is subjected to a similar distillation operation in a separate section on a smaller scale.

Using the method according to the invention it is for example possible to obtain lactic acid, which, after it has been heated for 2 hours under reflux, has a color of no more than 60 APHA units, preferably no more than 40 APHA units, and in particular no more than 5 APHA units. These APHA values are also attainable for other organic acids.

The invention will be further elaborated on the basis of the following Figures.

BRIEF DESCRIPTION OF THE FIGURES

FIG. 1 shows a flow scheme of the process according to the invention.

FIG. 2 shows diagrammatically a falling film evaporator.

FIG. 3 shows diagrammatically a wiped film evaporator.

FIG. 4 shows diagrammatically a short path evaporator.

DETAILED DESCRIPTION OF THE INVENTION

Figure 5A:
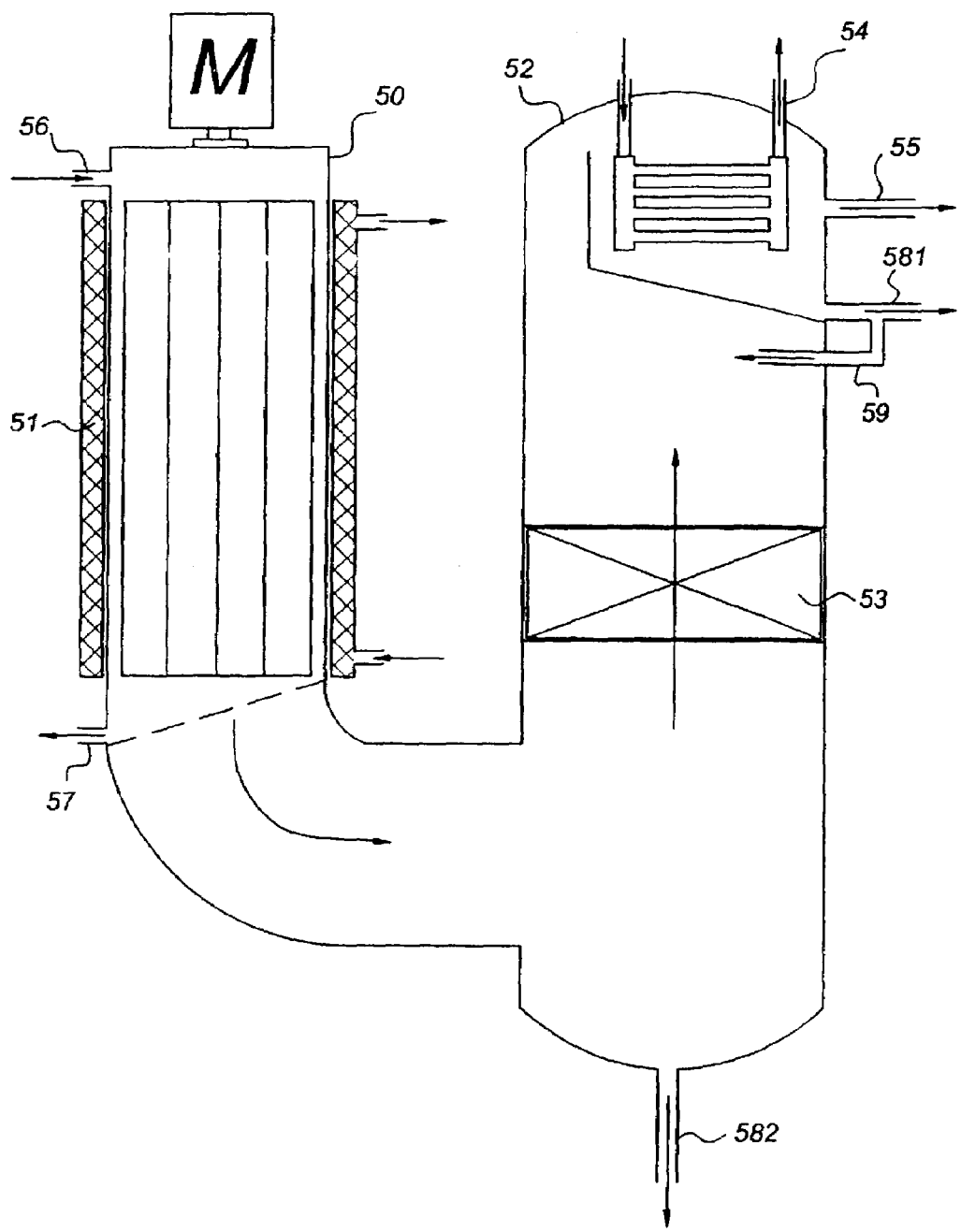
FIGS. 5A and 5B show diagrammatically a vacuum distillation unit according to the most preferred embodiments of the invention.

FIG. 1 shows a preferred embodiment of the method according to the invention. In this embodiment, a stream [1] of an aqueous solution of an organic acid having a boiling point at atmospheric pressure of less than 450° C., said steam [1] containing about 275 carboxylate ions/1 or less, is subjected to a first distillation step so as to form a bottom fraction [2] which substantially contains the organic acid and a top fraction [3] which substantially contains water. The bottom fraction [2] is preferably subjected to a "preflash" so as to form a top fraction [4] and a bottom fraction [5], the top fraction [4] substantially comprising water and the bottom fraction [5] substantially comprising the organic acid. The bottom fraction [5] is then subjected to a second distillation step, so as to form the top fraction [6] which substantially or entirely comprises the pure organic acid, and a bottom fraction (residue) [7]. This bottom fraction [7] is preferably subjected to a depolymerization step, in which an aqueous stream [10] is supplied which is preferably composed of the top fractions [3] and [4] and, if appropriate, additional water. The residue of the depolymerization step, stream [9], is discharged, and the product of the depolymerization step, stream [11], is further processed in one of the following ways:

1. purged [12],
2. processed in a separate distillation section as described above (hence, it comprises also two distillation steps and preferably also a prefab), although on a smaller scale [13], or
1. recycled to the first distillation step [14].

The invention also relates to a device for the purification of an aqueous solution of an organic acid having a boiling point at atmospheric pressure of less than 450° C. which comprises approximately 275 g/carboxylate ions/1 or less, preferably 250 g carboxylate ions/1 or less, and preferably less than 1% by weight ionic impurities, calculated on the basis of the total solution, the device comprising a first distillation device and a second distillation device.

According to a first preferred embodiment of the invention, a first distillation device comprises one or more film evaporation devices, such as falling film evaporators, wiped film evaporators and/or thin film evaporators, and one or more distillation columns, the distillation columns having a plate number of from 0.1 to 10, preferably 1 to 10, and in particular 1 to 5. The second distillation device preferably comprises a device which operates under vacuum (i.e. a device which can be operated at a pressure of from 0.01 to 50 mbar, more preferably 0.1 to 20 mbar, and in particular 1 to 10 mbar and more in particular 2 to 10 mbar), and this device comprises one or more short path evaporators or vacuum distillation units, preferably vacuum distillation units.

According to a second, but more preferred embodiment of the invention, the first and second distillation devices comprise one or more film evaporation devices, and one or more distillation columns, in which case the film evaporation devices may be falling film evaporators, wiped film evaporators and/or thin film evaporators, and in which case the distillation columns have a plate number of from 0.1 to 10, preferably 1 to 10, and in particular 1 to 5.

FIG. 2 diagrammatically depicts a falling film evaporator (an external condenser device is usually present, but it is not shown). A device of this type comprises a vessel [20] in which there are heater elements [21] through which a heating medium is passed via inlet and outlet openings [22] and [23]. The liquid which is to be evaporated is passed into the evaporator via inlet opening [24], the top fraction [25] containing the most highly volatile component(s), and the bottom fraction [26] containing the least volatile component(s). The top fraction is discharged to the external condenser device via vacuum line [27]. Any residue can be removed via outlet opening [28]. Drawbacks of falling film evaporators are that the laminator films which flow downwards along the heater elements give rise to so-called "hot spots", with the result that the product to be purified becomes overheated and is then decomposed. In the present case, "hot spots" of this type may lead to decomposition of the organic acid to thermal decomposition products and oligomerization of the organic acid. Other drawbacks of evaporators of this type is that the considerable temperature differences which prevail in the vessel do not allow optimum distillation results to be achieved and that the pressure in evaporators of this type cannot be lower than 20 mbar on account of the pressure drop which is caused by vapours which flow from the surface of the heater elements towards the external condenser device.

FIG. 3 diagrammatically depicts a wiped film evaporator. A device of this type comprises a vessel [30] and a heating jacket [31] through which a heating medium is passed via inlet and outlet openings [32] and [33]. An agitator [34] which is provided with paddles, wipers or scrapers, is arranged in the vessel, so that the liquid which is to be evaporated and is passed into the device via inlet opening [35] is dispersed over the wall of the heating jacket of the device as a film. The most highly volatile component(s) leave(s) the device via vacuum line [36] to an external condenser device, and the least volatile component(s) leave(s) via outlet opening [37]. The most significant drawback of wiped film evaporators is that the operating pressure window is minimal (only a few mbar), on account of the pressure drop of vapours which flow from the surface of the heater jacket to the external condenser device. Another drawback is that as the internal temperature falls, the pressure has to be reduced, leading to a considerable increase in the vapour volume and high flow resistances. The latter drawback can be overcome if an external condenser device is replaced by an internal condenser device which is arranged at a short distance from the wall of the heater jacket, so that in fact a short path evaporator is obtained.

A diagrammatic illustration of a short path evaporator is shown in FIG. 4. An evaporator of this type comprises a vessel [40], a heating jacket [41], a roller wiper system [42], which is driven by an external motor, for applying a film of the liquid which is to be evaporated, and an internal condenser device [43]. A heating medium is passed through the heater shell via inlet and outlet openings [441] and [442], while cooling water for the condenser device is passed through inlet and outlet openings [451] and [452]. The liquid which is to be evaporated is supplied to the evaporator via inlet opening [46]. The most highly volatile components are discharged via vacuum line [47], and the product is discharged via outlet line [48]. Advantages of a short path evaporator are in particular efficient heat transfer and the avoidance of "hot spots", the continuous operation of the distillation with a short residence time of the product which is to be purified on the wall of the heating jacket, and a working pressure which may be 0.01 bar. However, short path evaporators have the disadvantage that during operation splashing of the distilled product occurs against the internal condensor.

Figure 5B:
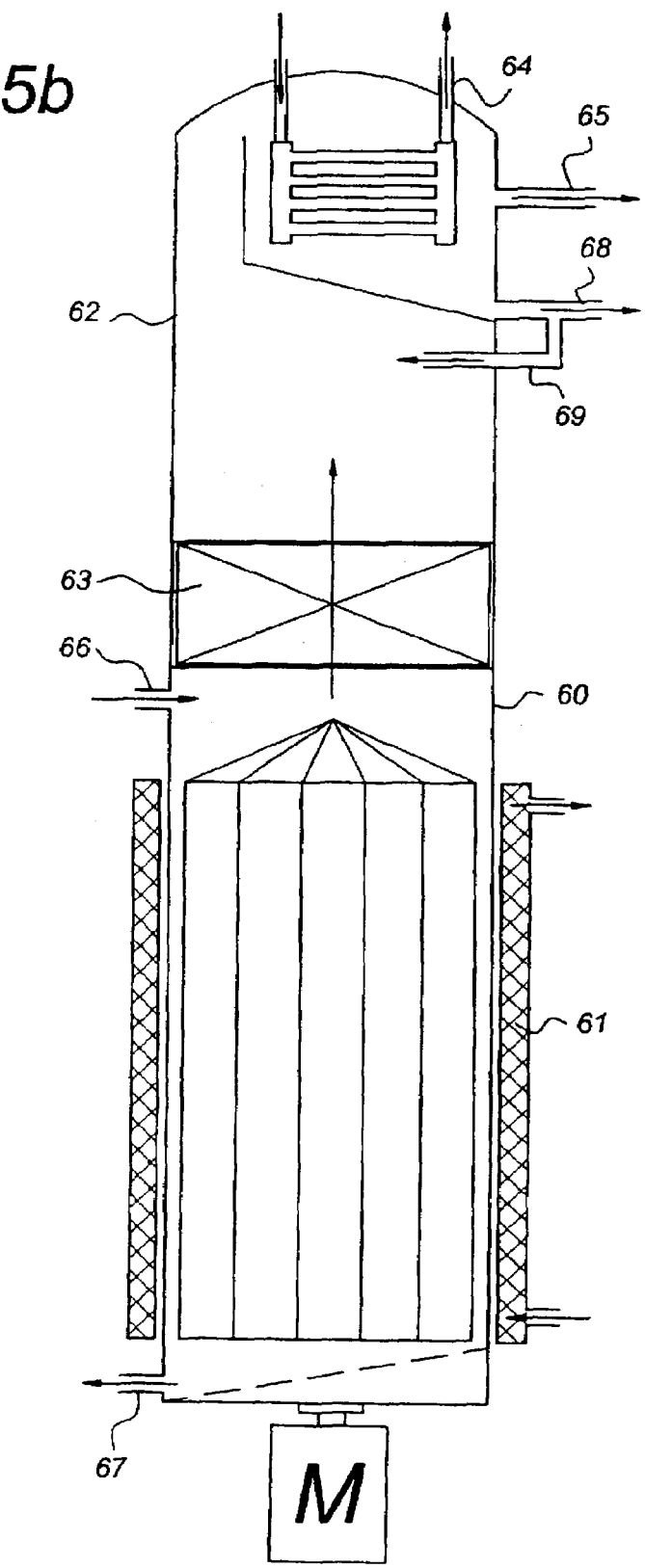

FIGS. 5A and 5B show vacuum distillation units according to the most preferred embodiment of the invention. These vacuum distillation units comprise a vessel [50, 60] for the evaporation of a film of the product which is to be evaporated, said vessel being provided with a heating jacket [51, 61], a feed inlet line [56, 66], a residue outlet line [57, 67], and a wiper system for providing a film of the product to be evaporated (not shown). The vapour is passed to a distillation column [52, 62]. The distillation column is provided with a packaging [53, 63], a cooling device [54, 64], a vacuum line [55, 65] and optionally a distribution plate (not shown) upstream of the packaging.

The distillation column preferably has a plate number of from 0.1 to 10, more preferably of 1 to 10 and in particular from 1 to 5. Vessel [50, 60] is preferably a falling film evaporator, a wiped film evaporator or a thin film evaporator, e.g. such as shown in FIGS. 2 and 3. Reflux conditions prevail in the distillation column [52, 62], so that optimum separation is brought about by means of distillation. This reflux is achieved by recycling product coming out of the product line [581, 68] via recycle line [59, 69] to the distillation column. The bottom product from the distillation column [57, 67], that in the present case contains the organic acid and impurities, is preferably recycled to the device [50, 60; not shown]. The top product [581, 581, 68] contains substantially pure organic acid. In the apparatus according to FIG. 5A, the vapour is separated into a less pure product (which leaves the distillation column via line [582]) and a more pure product (which leaves the distillation column via line [581]).

It has been found that the second distillation step can be more suitable carried out using a vacuum distillation unit as shown in FIGS. 5A and 5B instead of a short path distillation device.

Figure 6A:
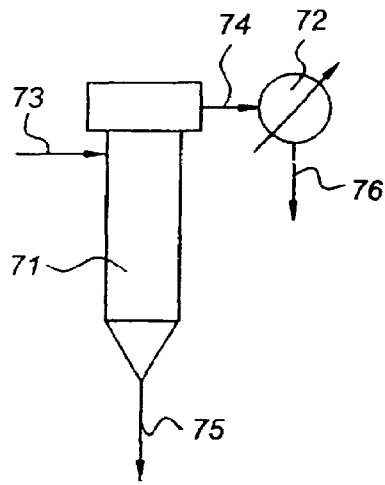
FIGS. 6A-6D show flow diagrams of preferred embodiments of the first distillation step.
Figure 6B:
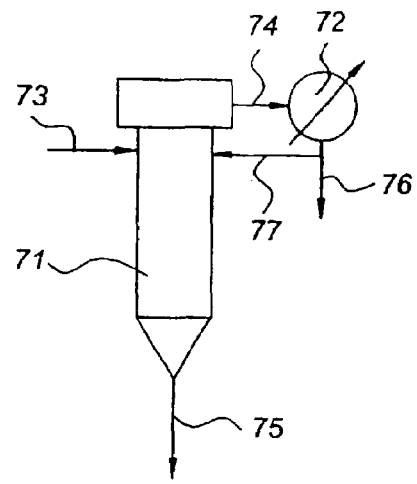
Figure 6C:
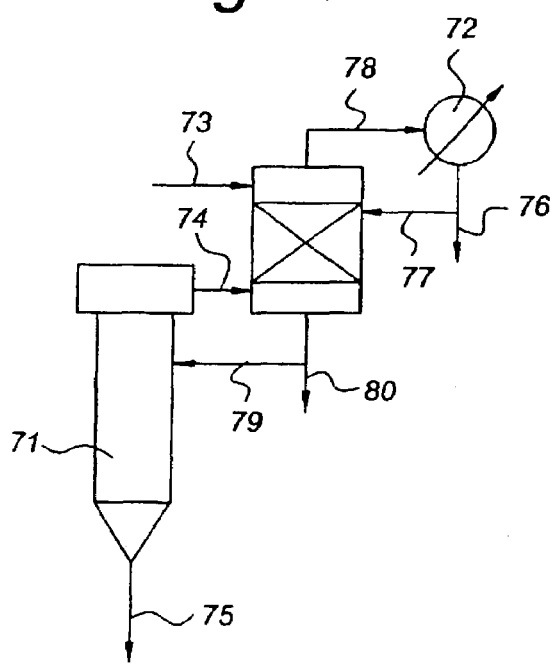
Figure 6D:
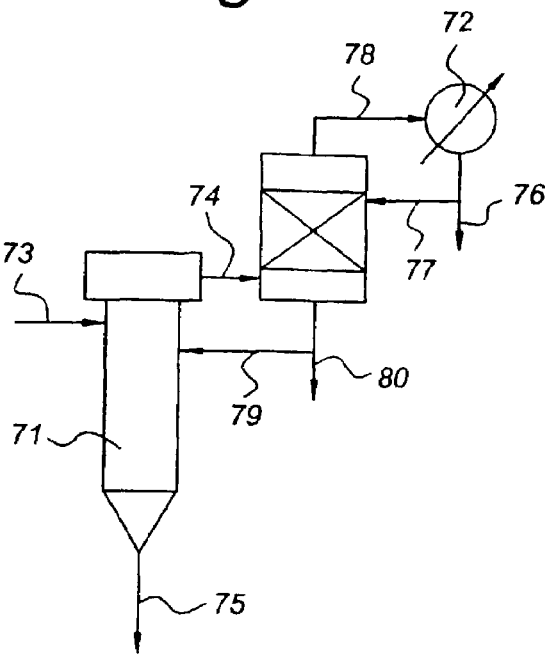

FIGS. 6A-6D show preferred embodiments of the first distillation step, wherein 6A shows the least preferred embodiment and 6C and 6D show the most preferred embodiments. As is outlined above, the first distillation step is conducted in a vessel [71] for evaporation of the product to be evaporated, i.e. a wiped film evaporator, a thin film evaporator or a falling film evaporator, and an external cooling device [72]. The feed enters the evaporator via feed inlet line [73] whereas the bottoms leaves the evaporator via bottoms exit line [75] and the evaporated product via product exit line [74]. The evaporated product is condensed in cooling device [72] and liquid product leaves the distillation unit via line [76]. As shown in FIG. 6B, part of the liquid product can be recycled to the evaporator via line [77] to maintain a reflux which, as is known by the skilled in the art, improves the separation. In FIG. 6C, the feed is introduced in distillation column via line [73], said distillation column being in open contact with evaporator [71] via line [74]. Due to the reflux conditions prevailing within the distillation column and within the evaporator (part or all of the bottoms leaving the distillation column via line [80] is recycled to the evaporator via line [79]), separation is established within the combination evaporator/distillation column. In FIG. 6D a modification of the configuration of FIG. 6C is shown, wherein the most important modification is that the feed is introduced into the evaporator instead of into the distillation column.

According to the invention, an aqueous solution of an organic acid having a boiling point at atmospheric pressure of less than 450° C. is therefore preferably purified in the following way:

(A) a first distillation step in which one or more falling film evaporators, wiped film evaporators and/or thin film evaporators are used, (B) a "preflash", (C) a second distillation device in which one or more short path devices and/or vacuum distillation units is/are used, and (D) a depolymerization step (if the organic acid can dimerize, oligomerize and/or polymerize).

More preferably, according to the invention the aqueous solution of the organic acid is purified in the following way (best mode of the invention):

(A) a first distillation step in which one or more falling film evaporators, wiped film evaporators, and/or thin film evaporators and one or more distillation columns are used, (B) a "preflash", (C) a second distillation device in which one or more short path distillation devices and/or vacuum distillation units is/are used, and (D) a depolymerization step (if the organic acid can dimerize, oligomerize and/or polymerize).

In particular, according to the invention an aqueous solution of lactic acid is purified in the following way:

(A) a first distillation step in which one or more falling film evaporators, wiped film evaporators and/or thin film evaporators and one or more distillation columns are used.

(B) a "preflash", (C) a second distillation device in which one or more vacuum distillation units is/are used, and (D) a depolymerization step (if the organic acid can dimerize, oligomerize and/or polymerize).

EXAMPLES

Colour Determination Of Lactic Acid

The method is based on ASTM D 5386-93. The colour of lactic acid is visually established by using a series of standard APHA solutions. Instead, the colour can be determined spectrofotometrically.

The standard solutions are prepared as follows. An amount of 1.245 g $K_2PtCl_6$ and 1.000 g of $CoC._2.6H_2O$ are dissolved in purified water. Subsequently, 100 ml 37% HCl is added and the solution obtained is diluted to 1000 ml by adding purified water. This stock solution (500 APHA) units) has to meet the following specifications:

| Wave length (nm) | Absorbance |
| --- | --- |
| 430 | 0.110-0.120 |
| 455 | 0.130-0.145 |
| 480 | 0.105-0.120 |
| 510 | 0.055-0.065 |

Thereafter, standard solutions are made of 5-300 APHA units with an interval of 5 APHA units by pipetting 1.0-60.0 ml of the stock solution in 100 ml volumetric flasks. Subsequently, the flasks are made up to 100 ml with purified water. When new solutions have to be made, the same flask must be used for the preparation of the same solution.

In the visual method, the colour of the lactic acid sample is determined abouve a light source using a 100 ml colorimetric tube where the standard APHA solutions are used as reference. In the spectrofotometric method, a base line is first established whereafter a calibration follows. Then, the absorbance of the lactic acid sample is determined and the APHA value is determined from the calibration table.

The Effect Of Splashing

Samples taken from a commercial plant that was either equipped with a short path evaporator (SPE) or a vacuum distillation unit (VDU) according to the invention were analyzed for their colour. Not only the colour of the neat sample was determined, but also after heating the sample for about two hours under reflux. The results are shown in Table I.

TABLE 1

| | Split | | Colour(APHA) | |
| --- | --- | --- | --- | --- |
| | Distillate | Residue | No heating | After heating |
| VDU | 80 | 20 | 20 | 34 |
| SPE | 75 | 25 | 40 | 60 |

The data show that at under almost identical operation conditions the VDU afforded a better product quality in terms of colour than the SPE.

The samples and the feed were further analysed for their $Ca^{2+}$ content. $Ca^{2+}$ was used as the parameter to determine splashing since it does not evaporate under the conditions of the method according to the invention. The splashing factor was calculated according to the following formula:

% splashing={$[Ca^{2+}]_{distillate}/[Ca^{2+}]_{feed}$}*100*0.75 wherein the number 0.75 stands for the split. The data are shown below in Table II. These data show that avoiding splashing (by using a VDU instead of a SPE) has a great advantageous effect on the product quality.

TABLE II

| VDU(with 90/10 split) | | | SPE(with 75/25 split) | | |
| --- | --- | --- | --- | --- | --- |
| $[Ca^{2-}]_{feed}$ (ppm) | $[Ca^{2-}]_{distillate}$ (ppm) | % Splashing | $[Ca^{2+}]_{feed}$ (ppm) | $[Ca^{2+}]_{distillate}$ (ppm) | % Splashing |
| 2180 | -(a) | 0.00 | 2749 | 36 | 0.98 |
| 1730 | -(a) | 0.00 | | | |
| 2440 | -(a) | 0.00 | | | |
| 5900 | -(a) | 0.00 | | | |
| 6172 | -(a) | 0.00 | | | |
| 6370 | 0.20 | 0.00 | | | |
| 3236 | -(a) | 0.00 | | | |
| 3840 | -(a) | 0.00 | | | |
| 14570 | 0.38 | 0.00 | | | |
| 6245 | -(a) | 0.00 | | | |
| 6532 | -(a) | 0.00 | | | |
| 23720 | -(a) | 0.00 | | | |
| 6402 | -(a) | 0.00 | | | |
| 5195 | -(a) | 0.00 | | | |
| 5510 | -(a) | 0.00 | | | |
| | | 0.00 (av.) | | | |

(a)the amount was below the detection limit of 0.03 ppm

The invention claimed is:

1. A method of purification comprising:
   (a) subjecting an aqueous solution of an organic acid having a boiling point at atmospheric pressure of less than 450° C. which comprises 275 g carboxylate ions/1 or less, calculated on the basis of the total solution, to a first and a second distillation step,
   (b) bringing the solution into vapor phase in the first distillation step by means of film evaporation, and
   (c) passing the vapor from (b) to a first distillation column.

2. The method according to claim 1, wherein the aqueous solution contains less than 1% by weight carboxylate ions, calculated on the basis of the total solution.

3. The method according to claim 1, wherein the organic acid is an α-hydroxy acid.

4. The method according to claim 1, wherein the acid is lactic acid.

5. The method according to claim 1, wherein the first distillation step is carried out at a temperature of from 80° to 150° C. and a pressure of from 50 to 250 mbar.

6. The method according to claim 5, wherein the temperature is between 100° and 140° C. and the pressure is between 60 and 150 mbar.

7. The method according to claim 1, wherein the film evaporation is wiped film evaporation, thin film evaporation or falling film evaporation.

8. The method according to claim 1, wherein the first distillation column has a plate number of from 0.1 to 10.

9. The method according to claim 1, wherein the first distillation step yields a bottom fraction comprising at least 95% by weight of Total Organic Acid, calculated on the basis of the weight of the bottom fraction.

10. The method according to claim 1, wherein the second distillation step is carried out at a temperature of from 80° to 200° C. and a pressure of from 0.01 to 50 mbar.

11. The method according to claim 10, wherein the temperature is between 100° and 200° C. and the pressure is between 0.1 and 20 mbar.

12. The method according to claim 1, wherein the second distillation step is carried out in at least one of a short path distillation device or vacuum distillation unit.

13. The method according to claim 12, wherein the second distillation is carried out in at least one vacuum distillation unit.

14. The method according to claim 1, wherein a product from the first distillation step is further brought into the vapor phase in the second distillation step by means of film evaporation, and the vapor is passed to a second distillation column.

15. The method according to claim 14, wherein the film evaporation comprises at least one of wiped film evaporation, thin film evaporation or falling film evaporation.

16. The method according to claim 14, wherein the first and/or second distillation column has a plate number from 0.1 to 10.

17. The method according to claim 1, wherein a product from the first distillation step is subjected to a conditioning step.

18. The method according to claim 1, wherein the second distillation step yields a residue, which residue is subjected to a depolymerization step to provide a product.

19. The method according to claim 18, wherein from 30 to 70% by weight of an aqueous stream and 70 to 30% by weight of the residue from the second distillation step, calculated on the basis of the weight of the residue, are mixed with one another and the mixture is heated at a temperature of from 60° to 100° C. for from 1 to 30 hours and under atmospheric pressure, the aqueous stream containing 80 to 100% by weight water, calculated on the basis of the weight of the aqueous stream.

20. The method according to claim 18, wherein the product obtained from the depolymerization step is purged and transferred to a second distillation column.

21. The method according to claim 18, wherein the product obtained from the depolymerization step is purged and returned to the first distillation step.

22. The method according to claim 1, wherein the method is carried out continuously.

23. The method according to claim 1, wherein a top fraction from the first distillation step substantially comprises water.

24. The method according to claim 1, wherein a top fraction from the first distillation step contains no more than 1% by weight organic acid.

25. A method of purification comprising:
 (a) subjecting a solution of a cyclic dimer of an organic acid having a boiling point at atmospheric pressure of less than 450° C. to a first and a second distillation step,
 (b) bringing the solution into the vapor phase in the first distillation step by means of film evaporation, and
 (c) passing the vapor from (b) to a distillation column.

26. The method according to claim 25, wherein the cyclic dimer is dilactide.

* * * * *

UNITED STATES PATENT AND TRADEMARK OFFICE
CERTIFICATE OF CORRECTION

| | | |
|---|---|---|
| PATENT NO. | : 7,410,556 B1 | Page 1 of 1 |
| APPLICATION NO. | : 10/130990 | |
| DATED | : August 12, 2008 | |
| INVENTOR(S) | : Winkelaar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 953 days.

Signed and Sealed this
Fourth Day of August, 2015

Michelle K. Lee
*Director of the United States Patent and Trademark Office*